(12) United States Patent
Robinson et al.

(10) Patent No.: US 8,188,346 B2
(45) Date of Patent: May 29, 2012

(54) COTTON VARIETY ST 4498B2RF

(75) Inventors: Michael Robinson, Greenville, MS (US); Randy Wood, Buckeye, AZ (US)

(73) Assignee: Bayer CropScience LP, Research Triangle Park, NC (US)

( * ) Notice: Subject to any disclaimer, the term of this patent is extended or adjusted under 35 U.S.C. 154(b) by 246 days.

(21) Appl. No.: 12/605,924

(22) Filed: Oct. 26, 2009

(65) Prior Publication Data

US 2010/0107274 A1 Apr. 29, 2010

Related U.S. Application Data

(60) Provisional application No. 61/197,375, filed on Oct. 27, 2008.

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. ........ 800/314; 800/260; 800/263; 800/264; 800/265; 800/278; 800/279; 800/300; 800/302; 435/421; 435/427

(58) Field of Classification Search .............. 800/260, 800/263, 264, 265, 278, 279, 300, 302, 314; 435/410, 421, 427
See application file for complete search history.

(56) References Cited

U.S. PATENT DOCUMENTS

| 6,818,807 B2 | 11/2004 | Trolinder et al. |
| 2006/0191046 A1* | 8/2006 | Reid et al. ............... 800/314 |
| 2009/0049564 A1 | 2/2009 | Burdett |

FOREIGN PATENT DOCUMENTS

| EP | 0 270 355 | 6/1988 |
| WO | WO 00/71733 | 11/2000 |

OTHER PUBLICATIONS

Briggs, F.N. and Knowles, P.F., "Introduction to Plant Breeding," Chapters 11, 13 & 18, Reinhold Publishing Corporation, (1967).
Sakhanoko, H.F. et al., "Induction of Somatic Embryogenesis and Plant Regeneration in Select Georgia and Pee Dee Cotton Lines," Crop Science, vol. 44, pp. 2199-2205 (2004).
Stam, P, "Marker-assisted Introgression: Speed at Any Cost?" Proceedings of the Eucarpia Meeting on Leafy Vegetable Genetics and Breeding, Noordwijkerhout, The Netherlands, Mar. 19-21, 2003. Eds, Th.J.L. van Hintutn, A. Lebeda, D. Pink, J.W. Schut. pp. 117-124 (2003).

\* cited by examiner

*Primary Examiner* — David T Fox
*Assistant Examiner* — Keith Robinson
(74) *Attorney, Agent, or Firm* — Hunton & Williams LLP

(57) ABSTRACT

The cotton variety ST 4498B2RF is disclosed. The invention relates to seeds, plants, plant cells, plant tissue, harvested products and cotton lint as well as to hybrid cotton plants and seeds obtained by repeatedly crossing plants of variety ST 4498B2RF with other plants. The invention also relates to plants and varieties produced by the method of essential derivation from plants of ST 4498B2RF and to plants of ST 4498B2RF reproduced by vegetative methods, including but not limited to tissue culture of regenerable cells or tissue from ST 4498B2RF.

30 Claims, No Drawings

COTTON VARIETY ST 4498B2RF

CROSS-REFERENCE TO RELATED APPLICATION

This application claims the benefit of U.S. Provisional Application No. 61/197,375, filed Oct. 27, 2008, the disclosure of which is herein incorporated by reference in its entirety.

BACKGROUND OF THE INVENTION (i) Field of the Invention

This invention relates to the field of plant breeding. More particularly, the invention relates to a variety of cotton designated as ST 4498B2RF, its essentially derived varieties and the hybrid varieties obtained by crossing ST 4498B2RF as a parent line with plants of other varieties or parent lines.

(ii) Description of Related Art

Cotton is an important, fiber producing crop. Due to the importance of cotton to the textile industry, cotton breeders are increasingly seeking to obtain healthy, good yielding crops of excellent quality.

Cotton is commonly reproduced by self-pollination and fertilization. This type of sexual reproduction facilitates the preservation of plant and variety characteristics during breeding and seed production. The preservation of these characteristics are often important to plant breeders for producing cotton plants having desired traits. Other methods of producing cotton plants having desired traits are also used and include methods such as genetic transformation via Agrobacterium infection or direct transfer by microparticle bombardment. Examples of such methods are disclosed, for example, in U.S. Pub. No. 20090049564, incorporated by reference herein in its entirety.

Due to the environment, the complexity of the structure of genes and location of a gene in the genome, among other factors, it is difficult to predict the phenotypic expression of a particular genotype. In addition, a plant breeder may only apply his skills on the phenotype and not, or in a very limited way, on the level of the genotype. As a result, a particular plant breeder cannot breed the same variety twice using the same parents and the same methodology. Thus, a newly bred variety is an unexpected result of the breeding process. Indeed, each variety contains a unique combination of characteristics.

By carefully choosing the breeding parents, the breeding and selection methods, the testing layout and testing locations, the breeder may breed a particular variety type. In addition, a new variety may be tested in special comparative trials with other existing varieties in order to determine whether the new variety meets the required expectations.

SUMMARY OF THE INVENTION

The invention relates to seeds, plants, plant cells, parts of plants, cotton lint or fiber, and cotton textiles of cotton variety ST 4498B2RF as well as to hybrid cotton plants and seeds obtained by crossing plants of ST 4498B2RF with other cotton plants. The invention encompasses plants and plant varieties produced by the method of derivation or essential derivation from plants of ST 4498B2RF and to plants of ST 4498B2RF reproduced by vegetative methods, including but not limited to regeneration of embryogenic cells or tissue of ST 4498B2RF. The invention also encompasses methods of producing cotton seeds that comprise crossing plants of cotton variety ST 4498B2RF either with itself or with a second, distinct cotton plant.

DETAILED DESCRIPTION OF THE PREFERRED EMBODIMENTS

The invention has been obtained by a general breeding process comprising the steps outlined below. For reference, see chapter 11, "Breeding Self-Pollinated Crops by Hybridization and Pedigree Selection," in Briggs and Knowles (1967).

Parent plants, which have been selected for good agronomic and fiber quality traits are manually crossed in different combinations. The resulting F1 (Filial generation 1) plants are self-fertilized and the resulting F2 generation plants, which show a large variability on account of optimal gene segregation, are planted in a selection field.

These F2 plants are observed during the growing season for health, growth vigor, plant type, plant structure, leaf type, stand ability, flowering, maturity, seed yield, boll type, boll distribution, boll size, fiber yield and fiber quality. Plants are then selected. The selected plants are harvested and the bolls analyzed for fiber characteristics and the seed cleaned and stored. This procedure is repeated in the following growing seasons, whereby the selection and testing units increase from individual plants in the F2, to multiple plant containing 'lines' (descending from one mother plant) in the F5 and the number of units decrease from approximately 2500 plants in the F2 to 20 lines in the F5 by selecting about 10-20% of the units in each selection cycle.

The increased size of the units, whereby more seed per unit is available, allows the selection and testing in replicated trials on more than one location with a different environment and a more extensive and accurate analyzing of the fiber quality.

The lines or candidate varieties become genotypically more homozygous and phenotypically more homogeneous by selecting similar plant types within a line and by discarding the so called off-types from the very variable F2 generation on to the final F7 or F8 generation.

Depending on the intermediate results the plant breeder may decide to vary the procedure described above, such as by accelerating the process by testing a particular line earlier or retesting a line another year. He may also select plants for further crossing with existing parent plants or with other plants resulting from the current selection procedure.

By the method of recurrent backcrossing, as described by Briggs and Knowles, supra, in chapter 13, "The Backcross Method of Breeding", the breeder may introduce a specific trait or traits into an existing valuable line or variety, while otherwise preserving the unique combination of characteristics of this line or variety. In this crossing method, the valuable parent is recurrently used to cross it at least two or three times with each resulting backcross F1, followed by selection of the recurrent parent plant type, until the phenotype of the resulting F1 is similar or almost identical to the phenotype of the recurrent parent with the addition of the expression of the desired trait or traits.

This method of recurrent backcrossing eventually results in an essentially derived variety, which is predominantly derived from the recurrent parent or initial variety. This method can therefore also be used to get as close as possible to the genetic composition of an existing successful variety. Thus, compared to the recurrent parent the essentially derived variety retains a distinctive trait, which can be any phenotypic trait, with the intention to profit from the qualities of that successful initial variety.

Depending on the number of backcrosses and the efficacy of the selection of the recurrent parent plant type and genotype, which can be supported by the use of molecular markers as described by P. Stam (2003), the genetic conformity with the initial variety of the resulting essentially derived variety may vary between 90% and 100%.

Other than recurrent backcrossing, as described herein, such essentially derived variety may also be obtained by the selection from an initial variety of an induced or natural occurring mutant plant, or of an occurring variant (off-type) plant, or of a somaclonal variant plant, or by genetic transformation of regenerable plant tissue or embryogenic cell cultures of the said initial variety by methods well known to those skilled in the art, such as Agrobacterium-mediated transformation as described by Sakhanokho et al., (2004), Reynaerts et al., (2000), Umbeck et al., (1988) and others. Examples of transgenic events transformed in this way are "LLCotton25," USDA-APHIS petition 02-042-01p, "Cot 102," USDA-APHIS petition 03-155-01 p, and "281-24-236," USDA-APHIS petition 03-036-01p combined with "3006-210-23," USDA-APHIS petition 03-036-02p. Information regarding these and other transgenic events referred to herein may be found at the U.S. Department of Agriculture's (USDA) Animal and Plant Health Inspection Service (APHIS) website. An "Event" is defined as a (artificial) genetic locus that, as a result of genetic engineering, carries a foreign DNA comprising at least one copy of the gene(s) of interest. Other methods of genetic transformation are well known in the art such as microprojectile bombardment. See, e.g., U.S. Publication No. 20090049564, which is incorporated by reference herein in its entirety.

The plants selected or transformed retain the unique combination of the characteristics of ST 4498B2RF, except for the characteristics (e.g., one, two, three, four or five characteristics) changed by the selection of the mutant or variant plant or by the addition of a desired trait via genetic transformation. Therefore, the product of essential derivation (i.e., an essentially derived variety), has the phenotypic characteristics of the initial variety, except for the characteristics that change as a result of the act of derivation. Plants of the essentially derived variety can be used to repeat the process of essential derivation. The result of this process is also a variety essentially derived from said initial variety.

In one embodiment, ST 4498B2RF progeny plants are produced by crossing plants of ST 4498B2RF with other, different or distinct cotton plants, and further selfing or crossing these progeny plants with other, distinct plants and subsequent selection of derived progeny plants. The process of crossing ST 4498B2RF derived progeny plants with itself or other distinct cotton plants and the subsequent selection in the resulting progenies can be repeated up to 7 or 8 times in order to produce ST 4498B2RF derived cotton plants.

ST 4498B2RF has been obtained by introducing the Event MON 88913 (APHIS petition 04-086-01p) via a cross between a donor plant containing this Event and the cotton variety ST 457. The F1 plants were backcrossed twice with variety ST 457. The resulting population F-BC2 expresses the characteristics of ST 457 combined with Event MON 88913. The Events MON 531 (USDA-APHIS petition 94-308-01p) and MON 15985 (USDA-APHIS petition 00-342-01p) were introduced in ST 457 by crossing the donor plant containing these Events with the cotton variety ST 457. The F1 plants were backcrossed twice with ST 457. The resulting backcross population B2-BC2 expresses the characteristics of ST 457 combined with the Events MON 531 and MON 15985. The Events were combined by crossing plants of F-BC2 with plants of B2-BC2 resulting in the ST 457 B2F BC3 population. Out of this population the variety ST 4498B2RF has been selected.

ST 4498B2RF is similar to the existing variety ST 457, but differs by its resistance to the insect pests Cotton Bollworm, Cotton Leafworm, Fall Armyworm, Pink Bollworm and Tobacco Budworm, as a result of the surprising expression of the Events MON 531 and MON 15985 in combination with the characteristics of ST 457 and the resistance to the herbicide glyphosate as a result of the surprising expression of the Event MON 88913 in combination with the characteristics of ST 457.

Provided herein as embodiments of the invention are seeds, plants, plant cells and parts of plants of the cotton variety ST 4498B2RF. Representative seeds of this variety will be deposited under rule 37 CFR 1.809, prior to issuance of a patent. Representative seeds of ST 4498B2RF will be deposited under ATCC Accession No. PTA-12489. Plants produced by growing such seeds are provided herein as embodiments of the invention. Also provided herein are pollen or ovules of these plants, as well as a cell or tissue culture of regenerable cells from such plants. In another embodiment, the invention provides for a cotton plant regenerated from such cell or tissue culture, wherein the regenerated plant has the morphological and physiological characteristics of cotton cultivar ST 4498B2RF, as described herein (e.g., Table 1), when grown in the same environmental conditions. In yet another embodiment, the invention provides methods of testing for a plant having the morphological and physiological characteristics of cotton cultivar ST 4498B2RF. In one embodiment, the testing for a plant having the morphological and physiological characteristics of cotton cultivar ST 4498B2RF is performed in the same field, under the same conditions and in the presence of plants of ST 4498B2RF, e.g., plants grown from the seed deposited under ATCC Accession No. PTA-12489. In another embodiment, the characteristics to be tested for are those described herein (e.g., Table 1).

In another embodiment, the present invention provides regenerable cells for use in tissue culture of cotton cultivar ST 4498B2RF. The tissue culture will preferably be capable of regenerating plants having the physiological and morphological characteristics of the cotton cultivar ST 4498B2RF, and of regenerating plants having substantially the same genotype as the cotton plant of the present invention. Preferably, the regenerable cells in such tissue cultures will be from embryos, protoplasts, meristematic cells, callus, pollen, leaves, anthers, pistils, roots, root tips, flowers, seeds, pods, bolls, or stems. Still further, the present invention provides cotton plants regenerated from the tissue cultures of the invention.

Yet another aspect of the current invention is a cotton plant of the cotton variety ST 4498B2RF comprising at least a first transgene, wherein the cotton plant is otherwise capable of expressing all the physiological and morphological characteristics of the cotton variety ST 4498B2RF. In particular embodiments of the invention, a plant is provided that comprises a single locus conversion. A single locus conversion may comprise a transgenic gene which has been introduced by genetic transformation into the cotton variety ST 4498B2RF or a progenitor thereof. A transgenic or non-transgenic single locus conversion can also be introduced by backcrossing, as is well known in the art. In certain embodiments of the invention, the single locus conversion may comprise a dominant or recessive allele. The locus conversion may confer potentially any desired trait upon the plant as described herein.

Single locus conversions may be implemented by backcrossing wherein essentially all of the desired morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

In a particular aspect, the invention provides for a method of introducing a single locus conversion into cotton cultivar ST 4498B2RF comprising: (a) crossing the ST 4498B2RF plants, grown from seed deposited under ATCC Accession No. PTA-12489, with plants of another cotton line that comprise a desired single locus to produce F1 progeny plants; (b) selecting F1 progeny plants that have the desired single locus to produce selected F1 progeny plants; (c) crossing the selected F1 progeny plants with the ST 4498B2RF plants to produce first backcross progeny plants; (d) selecting for first backcross progeny plants that have the desired single locus and the physiological and morphological characteristics of cotton cultivar ST 4498B2RF as described herein (e.g., Table 1), when grown in the same environmental conditions, to produce selected first backcross progeny plants; and (e) repeating steps (c) and (d) one or more times (e.g., one, two, three, four, etc., times) in succession to produce selected third or higher backcross progeny plants that comprise the desired single locus and all of the physiological and morphological characteristics of cotton cultivar ST 4498B2RF as described herein (e.g., Table 1), when grown in the same environmental conditions. Plants produced by this method have all of the physiological and morphological characteristics of ST 4498B2RF, except for the characteristics derived from the desired trait.

Another embodiment of the invention provides for a method of producing an essentially derived plant of cotton variety ST 4498B2RF comprising introducing a transgene conferring the desired trait into the plant, resulting in a plant with the desired trait and all of the physiological and morphological characteristics of cotton variety ST 4498B2RF when grown in the same environmental conditions. In another embodiment, the invention provides for a method of producing an essentially derived cotton plant from ST 4498B2RF comprising genetically transforming a desired trait in regenerable cell or tissue culture from a plant produced by the invention, resulting in an essentially derived cotton plant that retains the expression of the phenotypic characteristics of cotton variety ST 4498B2RF, except for the characteristics changed by the introduction of the desired trait.

Desired traits described herein include modified cotton fiber characteristics, herbicide resistance, insect or pest resistance, disease resistance, including bacterial or fungal disease resistance, male sterility, modified carbohydrate metabolism and modified fatty acid metabolism. Such traits and genes conferring such traits are known in the art. See, e.g., US 20090049564, incorporated by reference herein in its entirety.

The invention also provides for methods wherein the desired trait is herbicide tolerance and the tolerance is linked to a herbicide such as glyphosate, gluphosinate, sulfonylurea, dicamba, phenoxy proprionic acid, cyclohexanedione, triazine, benzonitrile, bromoxynil or imidazalinone. The invention also provides for methods wherein the herbicide tolerance is an expression of the Event "LLCotton25" and the insect resistance is an expression of the Event "281-24-236", Event "3006-210-23" or a combination thereof, or Event "Cot 102".

In one embodiment, the desired trait is insect resistance conferred by a transgene encoding a *Bacillus thuringiensis* (Bt) endotoxin, a derivative thereof, or a synthetic polypeptide modeled thereon.

Also included herein is a method of producing cotton seed, comprising the steps of using the plant grown from seed of cotton variety ST 4498B2RF, of which a representative seed sample will be deposited under ATCC Accession No. PTA-12489, as a recurrent parent in crosses with other cotton plants different from ST 4498B2RF, and harvesting the resultant cotton seed.

Another embodiment of this invention relates to seeds, plants, plant cells and parts of plants of cotton varieties that are essentially derived from ST 4498B2RF, being essentially the same as this invention by expressing the unique combination of characteristics of ST 4498B2RF, including the herbicide and insect resistance of ST 4498B2RF, except for the characteristics (e.g., one, two, three, four, or five characteristics) being different from the characteristics of ST 4498B2RF as a result of the act of derivation.

Another embodiment of this invention is the reproduction of plants of ST 4498B2RF by the method of tissue culture from any regenerable plant tissue obtained from plants of this invention. Plants reproduced by this method express the specific combination of characteristics of this invention and fall within its scope. During one of the steps of the reproduction process via tissue culture somaclonal, variant plants may occur. These plants fall within the scope of this invention as being essentially derived from this invention.

Another embodiment of the invention provides for a method of producing an inbred cotton plant derived from the cotton variety ST 4498B2RF comprising: (a) preparing a progeny plant derived from cotton variety ST 4498B2RF, a representative sample of seed of said variety having been deposited under ATCC Accession No. PTA-12489, by crossing cotton variety ST 4498B2RF with a cotton plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional 3-10 generations with sufficient inbreeding to produce an inbred cotton plant derived from the cotton variety ST 4498B2RF.

Another embodiment of this invention is the production of a hybrid variety, comprising repeatedly crossing plants of ST 4498B2RF with plants of a different variety or varieties or with plants of a non-released line or lines. In practice, three different types of hybrid varieties may be produced (see e.g., Chapter 18, "Hybrid Varieties" in Briggs and Knowles, supra): the "single cross hybrid" produced by two different lines, the "three way hybrid", produced by three different lines such that first the single hybrid is produced by using two out of the three lines followed by crossing this single hybrid with the third line, and the "four way hybrid" produced by four different lines such that first two single hybrids are produced using the lines two by two, followed by crossing the two single hybrids so produced. Each single, three way or four way hybrid variety so produced and using ST 4498B2RF as one of the parent lines contains an essential contribution of ST 4498B2RF to the resulting hybrid variety and falls within the scope of this invention.

The invention also provides for cotton lint or fiber produced by the plants of the invention, plants reproduced from the invention, and plants essentially derived from the invention. The final textile produced from the unique fiber of ST 4498B2RF also falls within the scope of this invention. The invention also provides for a method of producing a commodity plant product (e.g., lint, cotton seed oil) comprising obtaining a plant of the invention or a part thereof, and producing said commodity plant product therefrom.

The entire disclosure of each document cited herein (e.g., US patent publications, non-patent literature, etc.) is hereby incorporated by reference.

The invention will now be further described with reference to the following, non-limiting examples.

EXAMPLE 1

Seeds were obtained from plants finally selected in the process of breeding the new variety "ST 4498B2RF."

Seeds of the variety ST 4498B2RF, of which a representative sample will be deposited, were planted, together with seeds of cotton variety ST 4544B2RF as reference variety, in field trials at two locations: BCS Research Station, Edmonson, Tex. (see Table 1) and BCS Research Station Seaboard, NC (see Table 2).

Table 3 reflects the average expression of the characteristics of ST 4498B2RF. The sample that will be deposited represents the variety and this sample can be analyzed for the expression of its phenotypic characteristics at any time and at any location.

ST 4498B2RF has an indeterminate plant growth habit and has a strong, erect central stem. ST 4498B2RF is most similar to ST 4554B2RF; however, it has a stronger fiber and a significantly lower fiber micronaire as shown hereunder in Table 1 and 2:

TABLE 1

Individual Location Analysis from Edmonson, TX

| Entry Name | N | Yield | Lint % | Leu | Str | Mic | UR | Elong |
|---|---|---|---|---|---|---|---|---|
| ST 4498B2RF | 4 | 1895 | 0.43 | 1.13 | 28.2 | 3.8 | 82.9 | 11.9 |
| ST 4554B2RF | 4 | 1708 | 0.45 | 1.11 | 24.9 | 4.3 | 83.2 | 11.e6 |

TABLE 1-continued

Individual Location Analysis from Edmonson, TX

| Entry Name | N | Yield | Lint % | Leu | Str | Mic | UR | Elong |
|---|---|---|---|---|---|---|---|---|
| LSD(.05) | | 243 | 0.04 | 0.08 | 2.8 | 0.6 | 2.9 | 0.8 |
| CV (Error) | | 10.0 | 4.7 | 3.6 | 5.4 | 6.8 | 1.7 | 3.7 |
| Significance (Entry) | | 0.00 | 0.00 | 0.02 | 0.1 | 0.00 | 0.00 | 0.00 |
| Number Locations | 1 | 1 | 1 | 1 | 1 | 1 | 1 | |
| Total Reps | 2 | 2 | 2 | 2 | 2 | 2 | 2 | |

TABLE 2

Individual Location Analysis from Seaboard, NC

| Entry Name | N | Yield | Lint % | Len | Str | Mic | UR | Elong |
|---|---|---|---|---|---|---|---|---|
| ST 4498B2RF | 2 | 1312 | 0.39 | 1.13 | 31.0 | 4.2 | 83.1 | 11.2 |
| ST 4554B2RF | 2 | 923 | 0.39 | 1.11 | 29.7 | 5.0 | 82.8 | 11.3 |
| LSD(.05) | | 331 | 0.0 | 0.04 | 0.2 | 0.06 | 0.2 | 0.6 |
| CV (Error) | | 6.9 | 0.18 | 0.90 | 0.17 | 0.1 | 0.06 | 1.3 |
| Significance (Entry) | | 0.12 | 0.00 | 0.29 | 0.02 | 0.00 | 0.12 | 0.5 |
| Number Locations | 1 | 1 | 1 | 1 | 1 | 1 | 1 | |
| Total Reps | 2 | 2 | 2 | 2 | 2 | 2 | 2 | |

Moreover, as shown in Table 3, ST4498B2RF has a shorter plant length and more nodes at maturity compared to ST4554B2RF.

TABLE 3

Characteristics of ST 4498B2RF

| | | Variety | |
|---|---|---|---|
| Description of Characteristic | Possible Expression/Note | ST 4498B2RF | ST 4544B2RF |
| General Plant Type | | | |
| Plant Habit | spreading, intermediate, compact | Intermediate | Intermediate |
| Foliage | sparse, intermediate, dense | Intermediate | Intermediate |
| Stem Lodging | lodging, intermediate, erect | Erect | Erect |
| Fruiting Branch | clustered, short, normal | Normal | Normal |
| Growth | determinate, intermediate, indeterminate | Indeterminate | Indeterminate |
| Leaf color | greenish yellow, light green, medium green, dark green | Light Green | Light Green |
| Boll Shape | Length < Width, L = W, L > W | Length > Width | Length > Width |
| Boll Breadth | broadest at base, broadest at middle | Broadest at base | Broadest at base |
| Maturity Plant | date of 50% open bolls | | |
| cm. to first Fruiting Branch | from cotyledonary node | 12.1 | 12.7 |
| No. of nodes to 1st Fruiting Branch | excluding cotyledonary node | 6.2 | 5.4 |
| Mature Plant Height in cm. | cotyledonary node to terminal | 97.3 | 103.6 |
| Leaf: upper most, fully expanded leaf | | | |
| Type | normal, sub-okra, okra, super-okra | Normal | Normal |
| Pubescence | absent, sparse, medium, dense | Dense | Dense |
| Nectaries | present, absent | Present | Present |
| Stem Pubescence | glabrous, intermediate, hairy | Hairy | Hairy |
| General Plant Type | | | |
| Glands (Gossypol) | absent, sparse, normal, more than normal | | |
| Leaf | | Normal | Normal |
| Stem | | Sparse | Sparse |
| Calyx lobe | (normal is absent) | Normal | Normal |

TABLE 3-continued

Characteristics of ST 4498B2RF

| Description of Characteristic | Possible Expression/Note | Variety ST 4498B2RF | Variety ST 4544B2RF |
|---|---|---|---|
| Flower | | | |
| Petals | cream, yellow | Cream | Cream |
| Pollen | cream, yellow | Cream | Cream |
| Petal Spot | present, absent | Absent | Absent |
| Seed | | | |
| Seed Index | g/100 seed fuzzy basis | 10.1 | 9.8 |
| Lint Index | g lint/100 seeds | 6 | 6.4 |
| Boll | | | |
| Lint percent | | | |
| Gin Turnout, picked | | 0.4 | 0.4 |
| Number of Seeds per Boll | | 34.1 | 32 |
| Grams Seed Cotton per Boll | | 3.4 | 5.2 |
| Number of Locules per Boll | | 4 | 4 |
| Boll Type | storm proof, storm resistant, open | Open | Open |
| Fiber Properties | | | |
| Method HVI | | HVI | HVI |
| Length, inches, 2.5% SL | | 1.13 | 1.13 |
| Uniformity (%) | | 83.6 | 82.6 |
| Strength, T1 (g/tex) | | 29.8 | 29 |
| Elongation, E1 (%) | | 10.7 | 10.8 |
| Micronaire | | 4.2 | 4.5 |
| Diseases | | | |
| *Alternaria macrospora* | | NT | NT |
| Anthracnose | | NT | NT |
| *Ascochyta* Blight | | NT | NT |
| Bacterial Blight race 1 | | NT | NT |
| Bacterial Blight race 2 | | NT | NT |
| Bacterial Blight Race | | NT | NT |
| *Fusarium* Wilt | | NT | NT |
| *Phymatotrichum* Root Rot | | NT | NT |
| *Pythium* (specify species) | | NT | NT |
| *Rhizoctonia solani* | | NT | NT |
| Southwestern Cotton Rust | | NT | NT |
| General Plant Type | | | |
| *Thielayiopsis basicola* | | NT | NT |
| *Diplodia* Boll Rot | | NT | NT |
| Other (specify) | | | |
| *Verticillium* Wilt | | NT | NT |
| Nematodes, Insects, and Pests | | | |
| Root-Knot Nematode | | NT | NT |
| Boll Weevil | | NT | NT |
| Bollworm | | R | R |
| Cotton Aphid | | NT | NT |
| Cotton Fleahopper | | NT | NT |
| Cotton Leafworm | | NT | NT |
| Cutworm (specify species): | | NT | NT |
| Fall Armyworm | | MR | MR |
| Other (specify); | | | |
| *Reniform* Nematode | | NT | NT |
| Grasshopper (specify species) | | NT | NT |
| *Lygus* (specify species) | | NT | NT |
| Pink Bollworm | | R | R |
| Spider Mite (specify species) | | NT | NT |
| Stink Bug (specify species) | | NT | NT |
| Thrips (specify species) | | NT | NT |
| Tobacco Bud Worm | | R | R |

(NT = Not Tested, S = Susceptible, MS = Moderately susceptible, MR = Moderately Resistant, R = Resistant)

EXAMPLE 2

A variety has been essentially derived from ST 4498B2RF by the process of the transgression of the Event LLCotton 25, USDA-APHIS petition 02-042-01p, U.S. Pat. No. 6,818,807, into plants of the variety ST 4498B2RF via the method of recurrent backcrossing and selecting the plants which express the characteristics of ST 4498B2RF combined with the resistance to the herbicide glyfosinate.

EXAMPLE 3

A variety has been essentially derived from ST 4498B2RF by the process of the transgression of a gene construct via genetic engineering in regenerable cells or tissue of ST 4498B2RF and the subsequent selection of regenerated plants, which express the characteristics of ST 4498B2RF combined with the characteristic that results from the genetic transformation.

EXAMPLE 4

A variety that has been essentially derived from ST 4498B2RF by the selection of an induced or natural occurring mutant plant or off-type plant from plants of ST 4498B2RF, which plant retains the expression of the phenotypic characteristics of ST 4498B2RF and differs only from ST 4498B2RF in the expression of one, two, three, four, or five of the characteristics as listed in Table 1, when grown side by side with ST 4498B2RF on one or two locations in one or two growing seasons.

DEPOSIT INFORMATION

Applicant has deposited 2500 seeds of cotton variety ST 4498B2RF disclosed herein with the American Type Culture Collection (ATCC), 10801 University Boulevard, Manassas, VA 20110, USA, under ATCC Accession No. PTA-12489. The seeds were deposited with the ATCC on Feb. 3, 2012, under the Budapest Treaty. Access to this deposit will be available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer, and will be replaced if it becomes nonviable during that period. Applicant does not waive any rights granted under this patent or under the Plant Variety Protection Act (7 U.S.C. 2321 et seq.).

DEFINITIONS

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Cm to FFB: Measure of centimeters to first fruiting branch.

Crossing: The mating of two parent plants.

Cross-pollination: Fertilization by the union of two gametes from different plants.

Desired Agronomic Characteristics: Agronomic characteristics (which will vary from crop to crop and plant to plant) such as yield, maturity, pest resistance and lint percent which are desired in a commercially acceptable crop or plant. For example, improved agronomic characteristics for cotton include yield, maturity, fiber content and fiber qualities.

Diploid: A cell or organism having two sets of chromosomes.

Disease Resistance: The ability of plants to restrict the activities of a specified pest, such as an insect, fungus, virus, or bacterial.

Disease Tolerance: The ability of plants to endure a specified pest (such as an insect, fungus, virus or bacteria) or an adverse environmental condition and still perform and produce in spite of this disorder.

Donor Parent: The parent of a variety which contains the gene or trait of interest which is desired to be introduced into a second variety.

E1: Refers to elongation, a measure of fiber elasticity (high=more elastic).

Emasculate: The removal of plant male sex organs or the inactivation of the organs with a cytoplasmic or nuclear genetic factor conferring male sterility or a chemical agent.

Essentially all the physiological and morphological characteristics: A plant having essentially all the physiological and morphological characteristics means a plant having the physiological and morphological characteristics, except for the characteristics derived from the desired trait.

$F_1$ Hybrid: The first generation progeny of the cross of two nonisogenic plants.

Fallout (Fo): As used herein, the term "fallout" refers to the rating of how much cotton has fallen on the ground at harvest.

FB5 cm to FFN: Measure of centimeters from main stem to first fruiting node at fruiting branch 5.

2.5% Fiber Span Length: Refers to the longest 2.5% of a bundle of fibers expressed in inches as measured by a digital fibergraph.

Fiber Characteristics: Refers to fiber qualities such as strength, fiber length, micronaire, fiber elongation, uniformity of fiber and amount of fiber.

Fiber Elongation: Sometimes referred to as E1, refers to the elongation of the fiber at the point of breakage in the strength determination as measured by High Volume Instrumentation (HVI).

Fiber Span Length: The distance spanned by a specific percentage of fibers in a test specimen, where the initial starting point of the scanning in the test is considered 100 percent as measured by a digital fibergraph.

Fiber Strength (Str): Denotes the force required to break a bundle of fibers. Fiber strength is expressed in grams per tex on an HVI.

Fruiting Nodes: The number of nodes on the main stem from which arise branches that bear fruit or boll in the first position.

Genotype: The genetic constitution of a cell or organism.

Gin Turnout: Refers to fraction of lint in a machine harvested sample of seed cotton (lint, seed, and trash).

Haploid: A cell or organism having one set of the two sets of chromosomes in a diploid.

Length (Len): The fiber length in inches using an HVI.

Linkage: A phenomenon wherein alleles on the same chromosome tend to segregate together more often than expected by chance if their transmission was independent.

Lint Index: The weight of lint per seed in milligrams.

Lint Percent: The percentage of the seed cotton that is lint, handpicked samples.

Lint Yield: Refers to the measure of the quantity of fiber produced on a given unit of land. Presented below in pounds of lint per acre.

Lint/boll: As used herein, the term "lint/boll" is the weight of lint per boll.

Maturity Rating: A visual rating near harvest on the amount of open boils on the plant. The rating range is from 1 to 5, 1 being early and 5 being late.

Micronaire (Mic): Refers to a measure of fiber fineness (high=coarse fiber) as measured with an HVI machine. Within a cotton cultivar, micronaire is also a measure of maturity. Micronaire differences are governed by changes in perimeter or in cell wall thickness, or by changes in both. Within a variety, cotton perimeter is fairly consistent and maturity will cause a change in micronaire. Consequently, micronaire has a high correlation with maturity within a variety of cotton. Maturity is the degree of development of cell wall thickness.

Mr: Fiber maturity ratio.

Phenotype: The detectable characteristics of a cell or organism, which characteristics are the manifestation of gene expression.

Plant Height: The average height in meters of a group of plants.

Quantitative Trait Loci (QTL): Quantitative trait loci (QTL) refer to genetic loci that control to some degree numerically representable traits that are usually continuously distributed.

Recurrent Parent: The repeating parent (variety) in a backcross breeding program. The recurrent parent is the variety into which a gene or trait is desired to be introduced.

Regeneration: The development of a plant from tissue culture.

Seed/boll: Refers to the number of seeds per boll, handpicked samples.

Seedcotton/boll: Refers to the weight of seedcotton per boll, handpicked samples.

Seedweight: Refers to the weight of 100 seeds in grams.

Self-pollination: The transfer of pollen from the anther to the stigma of the same plant or a plant of the same genotype.

Single Locus Converted (Conversion) Plant: Plants which are developed by a plant breeding technique called backcrossing wherein essentially all of the desired morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

Stringout Rating: also sometimes referred to as "Storm Resistance" refers to a visual rating prior to harvest of the relative looseness of the seed cotton held in the boll structure on the plant. The rating values are from 1 to 5 (tight to loose in the boll).

Substantially Equivalent: A characteristic that, when compared, does not show a statistically significant difference (e.g., p=0.05) from the mean.

T1: A measure of fiber strength, grams per tex (high=stronger fiber).

Tissue Culture: A composition comprising isolated cells of the same or a different type or a collection of such cells organized into parts of a plant.

Transgene: A genetic locus comprising a sequence which has been introduced into the genome of a cotton plant by transformation.

Uniformity Ratio (Ur): The proportion of uniform length fibers. The uniformity ratio is determined by dividing the 50% fiber span length by the 2.5% fiber span length.

Vegetative Nodes: The number of nodes from the cotyledonary node to the first fruiting branch on the main stem of the plant.

CITED REFERENCES

Lawrence P. Burdett, "Cotton Variety 02T15," U.S. Pub. No. 20090049564.

F. N. Briggs, and P. F Knowles, 1967: "Introduction to Plant Breeding", Rheinhold Publishing Corporation.

H. F. Sakhanoko et al 2004: "Induction of Somatic embryogenesis and Plant Regeneration in Select Georgia and Pee Dee Cotton Lines", Crop Science 44: 2199-2205.

Umbecke et al 1988: "Genetic engineering of cotton plants and lines", Patent application number EP0290355.

Reynaerts et al 2000: "Improved method for Agrobacterium mediated transformation of cotton", Patent application number WO 0071733.

P. Stam, 2003: "Marker-assisted introgression: speed at any cost?" Proceedings of the Eucarpia Meeting on Leafy Vegetable Genetics and Breeding, Noordwijkerhout, The Netherlands, 19-21 Mar. 2003. Eds. Th. J. L. van Hintum, A. Lebeda, D. Pink, J. W. Schut. P117-124

Trolinder et al. "Herbicide tolerant cotton plants having event EE-GH1." U.S. Pat. No. 6,818,807 (2004).

What is claimed is:

1. A seed of cotton variety ST 4498B2RF, wherein a representative sample of seed of said variety was deposited under ATCC Accession No. PTA-12489.

2. A plant of cotton variety ST 4498B2RF, or a part thereof, wherein a sample of seed of said variety was deposited under ATCC Accession No. PTA-12489.

3. The plant part of claim 2, wherein said plant part is regenerable.

4. The plant part of claim 3, wherein said plant part is pollen, an ovule or a cell.

5. A tissue culture of regenerable cells of a plant of cotton variety ST 4498B2RF, or a part thereof, wherein a sample of seed of said variety was deposited under ATCC Accession No. PTA-12489.

6. The tissue culture of claim 5, wherein the regenerable cells are from embryos, meristematic cells, pollen, leaves, roots, root tips, anther, pistil, flower, seed, boll, or stem.

7. A cotton plant regenerated from the tissue culture of claim 5, wherein the regenerated cotton plant expresses all of the physiological and morphological characteristics of cotton variety ST 4498B2RF, a representative sample of seed of said variety having been deposited under ATCC Accession No. PTA-12489.

8. A method of producing cotton seed, comprising crossing the plant of claim 2 with itself or a second cotton plant.

9. The method of claim 8, wherein said method comprises crossing the plant of claim 2 with a second cotton plant.

10. An $F_1$ hybrid cotton seed produced by the method of claim 9.

11. An $F_1$ hybrid cotton plant produced by growing the seed of claim 10.

12. A method of producing a cotton plant having an added desired trait, wherein the method comprises introducing a transgene conferring the desired trait into the cotton plant of claim 2.

13. The method of claim 12, wherein the desired trait is at least one of male sterility, herbicide tolerance, insect or pest resistance, disease resistance, modified fatty acid metabolism, modified carbohydrate metabolism or modified cotton fiber characteristics.

14. The method of claim 13, wherein the desired trait is herbicide tolerance and the tolerance is conferred to an herbicide which is glyphosate, sulfonylurea, imidazolinone, dicamba, glufosinate, phenoxy proprionic acid, cyclohexanedione, triazine, benzonitrile, bromoxynil, or combinations thereof.

15. The method of claim 12, wherein the desired trait is insect resistance and the transgene encodes a *Bacillus thuringiensis* (Bt) endotoxin.

16. A cotton plant produced by the method of claim 12, wherein the plant comprises the desired trait and all of the physiological and morphological characteristics of cotton variety ST 4498B2RF when grown in the same environmental conditions.

17. A method of introducing a single locus conversion into cotton variety ST 4498B2RF comprising:
(a) crossing a plant of variety ST 4498B2RF, a representative sample of seed of said variety having been deposited under ATCC Accession No. PTA-12489, with a second plant comprising a desired single locus to produce F1 progeny plants;
(b) selecting F1 progeny plants that have the single locus to produce selected F1 progeny plants;
(c) crossing the selected progeny plants with at least a first plant of variety ST 4498B2RF to produce backcross progeny plants;
(d) selecting backcross progeny plants that have the single locus and physiological and morphological characteristics of cotton variety ST 4498B2RF to produce selected backcross progeny plants; and
(e) repeating steps (c) and (d) one or more times in succession to produce selected second or higher backcross progeny plants that comprise the single locus and otherwise comprise all of the physiological and morphological characteristics of cotton variety ST 4498B2RF when grown in the same environmental conditions.

18. The method of claim 17, wherein the single locus confers a trait, wherein the trait is at least one of male sterility, herbicide tolerance, insect or pest resistance, disease resistance, modified fatty acid metabolism, modified carbohydrate metabolism, modified cotton fiber characteristics, or combinations thereof.

19. The method of claim 18, wherein the trait is tolerance to an herbicide, wherein the herbicide is glyphosate, sulfonylurea, imidazolinone, dicamba, glufosinate, phenoxy proprionic acid, cyclohexanedione, triazine, benzonitrile, bromoxynil, or combinations thereof.

20. The method of claim 18, wherein the trait is insect resistance and the insect resistance is conferred by a transgene encoding a *Bacillus thuringiensis* endotoxin.

21. A cotton plant produced by the method of claim 17, wherein the plant has the desired single locus and all of the physiological and morphological characteristics of cotton variety ST 4498B2RF.

22. A method of producing an inbred cotton plant derived from the cotton variety ST 4498B2RF, the method comprising the steps of:
(a) preparing a progeny plant derived from cotton variety ST 4498B2RF, a representative sample of seed of said variety having been deposited under ATCC Accession No. PTA-12489, by crossing cotton variety ST 4498B2RF with a cotton plant of a second variety;
(b) crossing the progeny plant with itself or a second plant to produce a seed of a progeny plant of a subsequent generation;
(c) growing a progeny plant of a subsequent generation from said seed and crossing the progeny plant of a subsequent generation with itself or a second plant; and
(d) repeating steps (b) and (c) for an additional 3-10 generations with sufficient inbreeding to produce an inbred cotton plant derived from the cotton variety ST 4498B2RF.

23. A method of producing a commodity plant product comprising obtaining the plant or plant part of claim 2 and producing said commodity plant product therefrom.

24. The method of claim 23, wherein the commodity plant product is lint or cotton seed oil.

25. A cotton plant produced by growing the seed of claim 1.

26. A protoplast produced from the tissue culture of claim 5.

27. A method of producing a cotton plant having an added desired trait comprising introducing a transgene conferring the desired trait into the plant of claim 7.

28. A method of producing a cotton plant having an added desired trait comprising introducing a transgene conferring the desired trait into the plant of claim 25.

29. A cotton plant produced by the method of claim 27, wherein the plant comprises the desired trait and all of the physiological and morphological characteristics of cotton variety ST 4498B2RF when grown in the same environmental conditions.

30. A cotton plant produced by the method of claim 28, wherein the plant comprises the desired trait and all of the physiological and morphological characteristics of cotton variety ST 4498B2RF when grown in the same environmental conditions.

* * * * *